United States Patent
Fremerey (10) Patent No.: US 6,368,075 B1
(45) Date of Patent: Apr. 9, 2002

(54) PUMP WITH A MAGNETICALLY SUPPORTED ROTOR

(75) Inventor: Johan K. Fremerey, Bonn (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

(21) Appl. No.: 09/552,782

(22) Filed: Apr. 20, 2000

(30) Foreign Application Priority Data

| Apr. 20, 1999 | (DE) | 19918841 |
|---|---|---|
| Apr. 20, 1999 | (DE) | 29907332 |
| Sep. 18, 1999 | (DE) | 19944863 |

(51) Int. Cl.[7] .......... F04B 35/00; F04B 17/00; F04B 35/04; H02K 7/09
(52) U.S. Cl. .......... 417/365; 417/352; 417/423.12; 417/310; 417/90.5
(58) Field of Search .......... 417/352, 365, 417/423.12; 310/90.5

(56) References Cited

U.S. PATENT DOCUMENTS

| 3,512,851 A | 5/1970 | Love | |
| 3,614,181 A | * 10/1971 | Meeks | 308/10 |
| 3,623,835 A | 11/1971 | Boyd | |
| 4,057,369 A | * 11/1977 | Isenberg et al. | 417/365 |
| 4,398,773 A | 8/1983 | Boden et al. | |
| 4,688,998 A | * 8/1987 | Olsen et al. | 417/356 |
| 4,763,032 A | * 8/1988 | Bramm et al. | 310/90.5 |
| 4,779,614 A | * 10/1988 | Moise | 600/16 |
| 4,812,694 A | 3/1989 | Fremerey | |
| 4,948,348 A | * 8/1990 | Doll et al. | 417/365 |
| 5,126,610 A | 6/1992 | Fremerey | |
| 5,211,546 A | 5/1993 | Isaacson et al. | |
| 5,385,581 A | 1/1995 | Bramm et al. | |
| 5,695,471 A | 12/1997 | Wampler | |

FOREIGN PATENT DOCUMENTS

| DE | 24 44 099 A1 | 4/1976 | F16C/32/04 |
| DE | 25 37 367 C3 | 4/1976 | F16C/32/04 |
| DE | 24 57 78 3 C2 | 6/1976 | F16C/32/04 |
| DE | 29 19 236 A1 | 5/1979 | F16C/32/04 |
| EP | 0 856 666 A1 | 8/1998 | F04D/3/02 |
| EP | 0 882 427 A1 | 12/1998 | A61B/8/12 |
| GB | 2 057 590 | 4/1981 | F16C/39/06 |
| GB | 2 088 017 A | 6/1982 | F16H/25/22 |
| WO | WO 92/15795 | 9/1992 | F16C/39/06 |

OTHER PUBLICATIONS

"A Fluid Dynamic Analysis Using Flow . . . " by Wernicke et al. (Artificial Organs (19(2)–161–177, 1995).

* cited by examiner

Primary Examiner—Charles G. Freay
Assistant Examiner—Timothy P. Solak
(74) Attorney, Agent, or Firm—Herbert Dubno (57) ABSTRACT

A tube pump in which the rotor is axially supported by permanent magnets at each end, so arranged as to apply attractive force across the gap between the rotor and a stator such that permanent magnets provide the sole radial support for the rotor. The axially effective permanent magnets are provided in conjunction with an electromagnetic stabilizer restoring the axial position of the rotor upon a shaft toward one or the other of the opposite ends thereof.

23 Claims, 5 Drawing Sheets

PUMP WITH A MAGNETICALLY SUPPORTED ROTOR

FIELD OF THE INVENTION

The invention relates to a pump for fluids, whereby under a fluid both a gas and a liquid is to be understood.

BACKGROUND OF THE INVENTION

For the displacement of sensitive liquids like especially blood, pumps have been developed in which a rotor is held in an equilibrium position within a support tube by mechanical field forces. Thus a blood pump is known from U.S. Pat. No. 5,695,471 which is configured as a radial pump with a radial rotor. The radial rotor is disposed within a support tube and has, in an inlet side projection, a plurality of rotor magnets which are juxtaposed with stator magnets on the support tube. Additionally, the radial rotor has distributed about its periphery a plurality of rod-shaped rotor magnets extending in axial direction and which are juxtaposed with ring-shaped stator magnets displaced on both sides of the radial rotor along the sides of the support tube. These rotor and stator magnets should support the radial journaling in the region of the projection of the rotor. The rotor is held purely mechanically in the axial direction at one end by a ball and at its opposite end on a point bearing.

The rotor is driven by means of a brushless rotary field or three phase motor. For this purpose, on sides of the support tube a coil is provided which cooperates with a spoked pole magnet set into the radial rotor. The drawback with this blood pump is that the journaling stability in the radial direction is not optimal and the pump, because of the multiplicity of rotor and stator magnets, requires considerable space and has a high weight. In addition, the purely mechanical bearing in the axial direction suffers from wear which is especially a disadvantage for implanted blood pumps.

Axial pumps are also known for use as blood pumps. In this case, the journaling is effected exclusively mechanically in guide wheels which are arranged at fixed locations in the support tube ahead of and behind the rotor. (Wernicke et al., A Fluid Dynamic Analysis Using Flow Visualization of the Baylor/NASA Implantable Axial Flow Blood Pump for Design Improvement, Artificial Organs 19(2), 1995, Pages 161–177). Such mechanical bearings are wear intensive and have in addition an unsatisfactory influence on sensitive liquids, especially body liquids like blood. Rotor devices with mechanically journaled rotors have been developed as well for measuring devices. Thus in German patent document 29 19 236 a turbine wheel counter is described for measurement of the flow of liquids, in which the rotor has two spaced-apart rotor magnets for radial stability which are configured as permanent magnets and are juxtaposed pairwise with stator magnets surrounding the support tube and also formed as permanent magnets. Thus the rotor and stator magnets are magnetized to repel each other in axial direction.

Between the stator magnets, an electric magnet coil is arranged which annularly surrounds the support tube. The magnet coil cooperates with a ferromagnetic flux conductive piece on the rotor which is arranged between the rotor magnets. In addition, a sensor is provided which detects the axial position of the rotor and cooperates with a control device which regulates the electric current in the magnetic coil. As soon as the field forces of the rotor and stator magnets determine that an axial shift of the rotor has occurred, the rotor is accelerated from the equilibrium position in the axial direction and the rotor, by measurement of the axial shift of the rotor, generates a signal which is effective to produce a counteracting, stabilizing field force in the magnetic coil. The rotor thus responds to an axial position shift in one or another of the devices to continuously return the rotor in one or the other direction upon an axial position shift. Thus the stabilizing axial force is so phaseshifted with respect to an axial position change that the rotor is both restored in position and is also shifted into its setpoint position by damping forces.

A drawback of the aforedescribed rotor device resides in that the rotor has only a relatively small bearing stiffness in the radial direction. The origin thereof is the distance between the stator and rotor magnets because of the annular channel provided between the carrier tube and the rotor and along which the fluid is displaced.

In German patent document DE-A-24 44 099, a magnetic bearing for rapidly moving bodies is known. This magnetic bearing has a rotor whose ends are provided with pole positions lying opposite one another and having permanent magnets and which apply attractive forces to the rotor to hold it in a stable position. By means of a contactless position sensing, deviations can be determined from the equilibrium position. Such devices are compensated by a powerless electromagnetic stray field control for which annular coils are provided which are arranged at the pole pieces proximal to the gaps with the rotor. Such a magnetic bearing is not suitable in a support tube through which a fluid is guided on spatial grounds.

OBJECT OF THE INVENTION

The invention has as its object to provide a pump of the aforedescribed type which has significantly higher bearing stiffness, especially in the radial direction and which permits highly versatile use thereof.

SUMMARY OF THE INVENTION

These objects are attained in accordance with the invention by the following features:

a) the pump has a support tube;

b) in the support tube a rotor is rotatably journaled;

c) the rotor has displacement elements for conveying the fluid through the support tube;

d) the rotor has at both ends axially magnetized permanently magnetic rotor magnets;

e) the ends of the rotor are juxtaposed with axially-opposite permanently magnetic stator magnets connected with the support tube;

f) each stator magnet has such axial magnetization that the neighboring stator and rotor magnets opposite one another attract each other;

g) the pump has a magnetic axial stabilizing unit for the rotor; and h) the pump has an electric motor with a stator generating a rotary field on the support tube and a spoked pole magnet on the rotor.

The object is also attained by a pump with the following features:

a) the pump has a support tube;

b) a rotor is rotatably journaled in the support tube;

c) a rotor has displacement elements for conveying the fluid through the support tube;

d) on the ends of the rotor there are each an axially-magnetized permanently magnetic magnet and a flux guide piece opposite one another, whereby the magnets are either on the rotor as rotor magnets or are connected with the support tube (2) as stator magnets;

e) the pump has a magnetic axial stabilizer unit; and f) the pump has an electric motor with a rotary field generating stator on the support tube and a spoked pole magnet on the rotor.

The basic concept of the invention is thus, by means of rotor and stator magnets in an end orientation, to generate a magnetic field bridging the gap between rotor and stator magnets in the axial direction so that the respective opposing pairs of rotor magnets and stator magnets oppositely attract one another. As a result, the bearing stiffness with the same geometry of the magnetic bearing of DE-A-29 19 236 is increased by at least the power of ten, without affecting significantly the annular channel between the support tube and the rotor hub.

The aforedescribed effect also arises when two magnets, i.e. rotor and stator magnets, are not juxtaposed with one another but rather at each end a magnet on one side and the flux guide piece on the other side are used. Thus the magnets can alternatively be used as rotor magnets which are affixed to the rotor and the flux-conducting pieces connected to the support tube or the flux-conductive pieces can be arranged on the rotor and the magnets can be seated on the support tube as stator magnets. For producing a high bearing stiffness, additional electric magnetic coils can be provided for reinforcing the magnetization of the flux-conducting pieces in the sense of increasing the attractive force between the magnet and the flux-conducting pieces.

To the extent pairwise rotor and stator magnets are juxtaposed with one another they preferably are comprised of at least two interfitting partial magnets whereby the respective radial neighboring partial magnets are oppositely magnetized. With this configuration of the rotor and stator magnets, the bearing stiffness can be increased by around a factor of 40.

The rotor is advantageously configured as an axial rotor so that it can serve as an axial pump. Such an axial rotor is substantially less expensive to produce than a radial rotor.

According to the invention, the rotor has a rotor hub and the rotor magnets or flux-guide pieces are arranged in the rotor hub, whereby the stator magnets or the flux guide pieces are disposed opposite the ends of the rotor hub. The stator magnets or flux guide pieces can be connected to the support tube with webs or ribs which are conducive to flow. Because of this arrangement, a compact construction is provided and detrimental cracks are avoided to the greatest possible extent. The stator magnets or flux guide pieces should be arranged in radial stabilizers whose contours do not project beyond the rotor hub, whereby the radial stabilizers preferably have the same contours as the rotor hub.

In a further feature of the invention it is provided that the respective opposite ends of the radial stabilizer and the rotor are so configured that at least one is of spherical shape. Because of this feature, a mechanical engagement of regions remote from the axis of the rotor and the radial stabilizer are avoided upon axial deflection of the rotor. For limiting the radial and/or axial mobility of the rotor it is advantageous that the respective end faces of the radial stabilizer and the rotor be formed with interfitting complementary bearing pins and bearing recesses, whereby a corresponding radial play is ensured in that the bearing pin and recess only come into contact with relatively large deflections of the rotor in the radial direction. In a further feature, the invention provides that the rotor magnets and the stator magnets are arranged directly opposite one another, respectively, and thereby produce the strongest possible magnetic field.

According to the invention the axial stabilizing device have at least one electric magnet coil as well as a control unit with a sensor for the axial movement of the rotor, whereby the control unit influences the electric current flow in the magnet coil or the magnet coils so that the magnetic field of the magnetic coil or coils counters an axial movement of the rotor from its setpoint position. Such an axial stabilizing device is known in principle from DE-A-29 19 236 and DE-A-24 44 099 and has been found to be effective. There are two possibilities for the arrangement of the magnet coils, namely, one in which the coils are on the support tube in such manner that they surround the support tube, and the other in which they are located in the radial stabilizers themselves whereby precautions must be taken for leading out the conductors to and from the magnet coils. Preferably the radial stabilizers have flux-conducting pieces in such configuration and disposition that the axial magnetic field generated by the rotor and stator magnets are superimposed in the gap between the ends of the radial stabilizers and rotor by the magnetic field generated by the magnetic coil in the axial direction and, indeed, in such manner that an axial movement of the rotor out of its intended position is counteracted. The magnetic coils themselves can be used as sensors. The flux-conducting pieces are preferably disposed at the level of the magnetic coils.

To the extent that a speed determination is desired, it is advantageous to provide the rotor with a pulse generator and support tube with a pulse pickup so that the pulse generator produces pulses for the pulse pickup corresponding to the speed of the rotor. This can be achieved simply by configuring the pulse generator magnetic as magnetic pulse source and the pulse pickup as a coil. In the coil, upon rotation of the rotor, an electric current is induced.

In a further aspect of the invention it is provided that the electric motor have at the level of the rotor a rotary field stator excitable with polyphase three-phase-alternating current and to provide the rotor so that it has a radially-magnetized spoked pole magnet. The result is a synchronous motor which, upon excitation of the rotary field stator with three phase current, produces a rotating field which entrains the rotor so that rotary movement is imposed upon the rotor. The rotary unit has, therefore, motor characteristics and can be used not only for measurement purposes but also as a pump for the displacement of fluids depending upon the rotor configuration. Preferably the spoked pole magnet has at least four magnetic segments magnetized in different radial directions. This construction counteracts wobbling movement of the rotating rotor which can arise because of magnetic field asymmetry in regions of the bearing gap between rotor and radial stabilizer. The rotary field stator should be connected with an electronic three-phase generator permitting load angle regulation. The targeted regulation of the load angle both with respect to magnitude and direction allows adjustment of the rotary field or the torque and stabilization of the rotor.

The rotor is matched to the respective use. Thus the rotor can have displacement elements in the form of wing-like projections. It can however also be provided with at least one helical rib so that, between the individual turns of the rib, channels are provided which effect the displacement. Pumps of this type can be used for generating high vacuums.

Alternatively, a blade crown can be formed on the rotor hub and can overlap with a complementary scoop-shaped blade crown on the inner wall of the support tube. Depending upon the configurations of the respective blade crowns, the pump can have various use possibilities, for example, as a gas turbine or high-vacuum pump. The aforedescribed blade crown configuration can also be combined with helically oriented channels. In this manner a so-called compound pump for use in vacuum technology and with an especially high compression ratio can be made.

SPECIFIC DESCRIPTION

Figure 1:
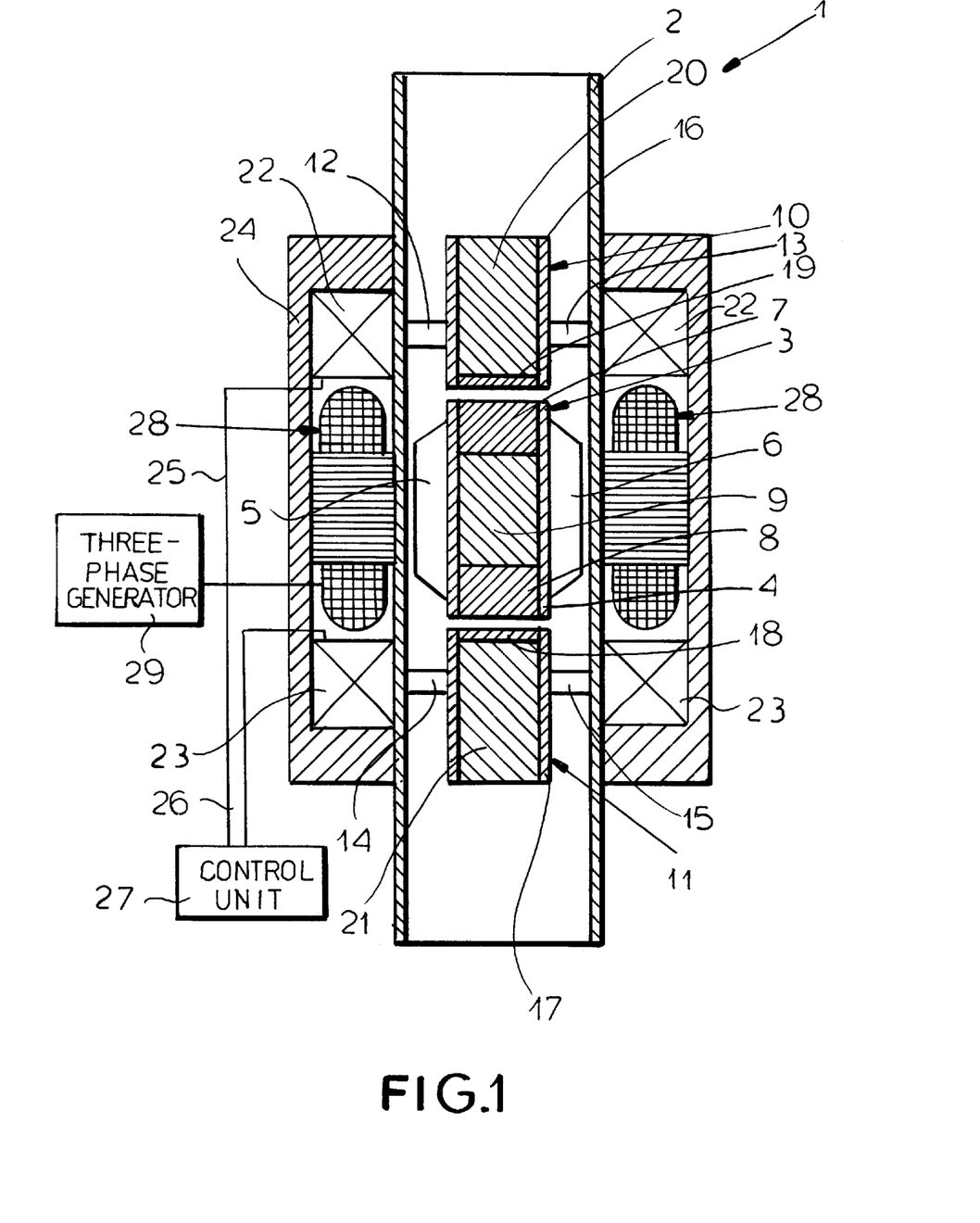
FIG. 1 is a longitudinal section through the pump of the invention.

FIG. 1 shows a pump designated as a whole at 1 for incorporation in a liquid or gas supply pipe. The pump 1 has a cylindrical support tube 2 which, via flanges not shown, can be incorporated as an intermediate piece in the pipe so that the liquid or the gas flows to the support tube 2.

Within the support tube 2 there is centrally disposed a rotor 3 which has a cylindrical rotor hub 4 and is formed on its exterior with vanes 5, 6. The vanes 5, 6 are so configured that the liquid in the annular channel between the rotor 3 and the support tube 2 is displaced axially by the rotor 3. In the end regions, the rotor hub 4 has two rotor magnets 7, 8 which are configured as permanent magnets and are axially magnetized. Between both rotor magnets 7, 8, a spoked pole magnet 9 is disposed which is magnetized into four radial directions distributed over the periphery.

Neighboring the two ends of the hub 4 radial stabilizers 10, 11 are provided which via ribs 12, 13, 14,15 are so affixed to the inner side of the support tube 2 and are coaxial with the rotor 3 that they lie axially symmetrical to the rotor 3. The radial stabilizers 10, 11 have cylindrical stabilizer sleeves 16, 17 whose diameters correspond to the diameter of the rotor hub 4. The radial stabilizers 10, 11 also form, with respect to their outer contours, extensions of the rotor hub 4. The stabilizer sleeves 16, 17 enclose stator magnets 18 and 19 which are respectively formed as permanent magnets in the region adjacent the rotor 3, whereby the stator magnets 18, 19 are so axially magnetized that in the gaps between the radial stabilizers 10, 11 and the rotor 3 an axially directed magnetic field is produced which is attractive to the rotor 3. These magnetic fields serve to hold the rotor 3 centrally of the axis of the support tube 2 and thus restore possible radial deviations. As a result a high bearing stiffness is generated in the radial direction.

The radial stabilizers 10, 11 have additional ferromagnetic flux guide pieces 20, 21 which cooperate with ring-shaped electric magnet coils 22, 23 of an axial stabilizing device. The magnet coils 22,23 are arranged at the level of the flux guide pieces 20, 21 and externally surround the support tube 2. They are located within the housing 24 annularly surrounding the support tube 2 and which, in the end regions simultaneously serves as a flux guide piece for the magnet coils 22, 23. The two magnet coils 22, 23 are connected via electric conductors 25, 26 with a control unit 27. The control unit 27 feeds the magnet coils 22, 23 with excitation current.

As a result, the magnetic flux in the gap between the rotor 3 and radial stabilizers 10, 11 are so superimposed and controlled that the rotor 3 assumes an axially stable position, contactless on all sides, between the radial stabilizers 10, 11. Thus the magnetic coils 22, 23 are used not only for flux regulation but simultaneously also as sensor coils for the contactless detection of the axial position of the rotor as this is done in the same way for the magnetic bearing of DE-A-24 44 099.

Between two magnet coils 22, 23, an annular rotary field or three-phase stator 28 is provided in the housing 24 and together with the spoked pole magnet 9 in the rotor 3 forms a synchronous motor. The rotary field stator is connected, for this purpose, with an electronic three-phase generator 29. This can excite the three-phase stator 28 with three-phase current whereby the desired control of the load angle both as to magnitude and direction, allows the torque effective on the rotor to be adjusted and the rotor stabilized.

Figure 2:
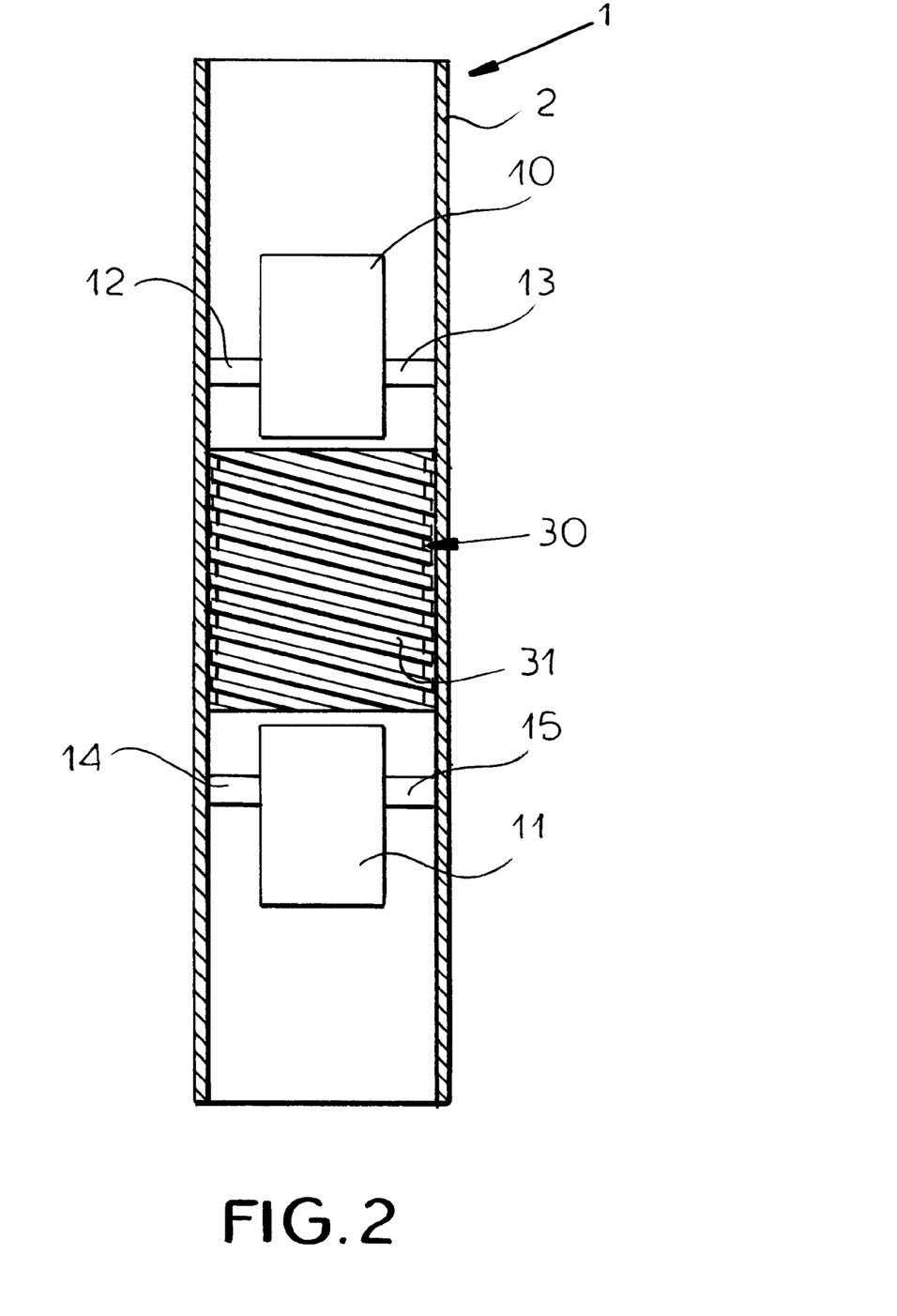
FIG. 2 is a longitudinal section through the combination of support tube and rotor in a second embodiment for a pump.
Figure 3:
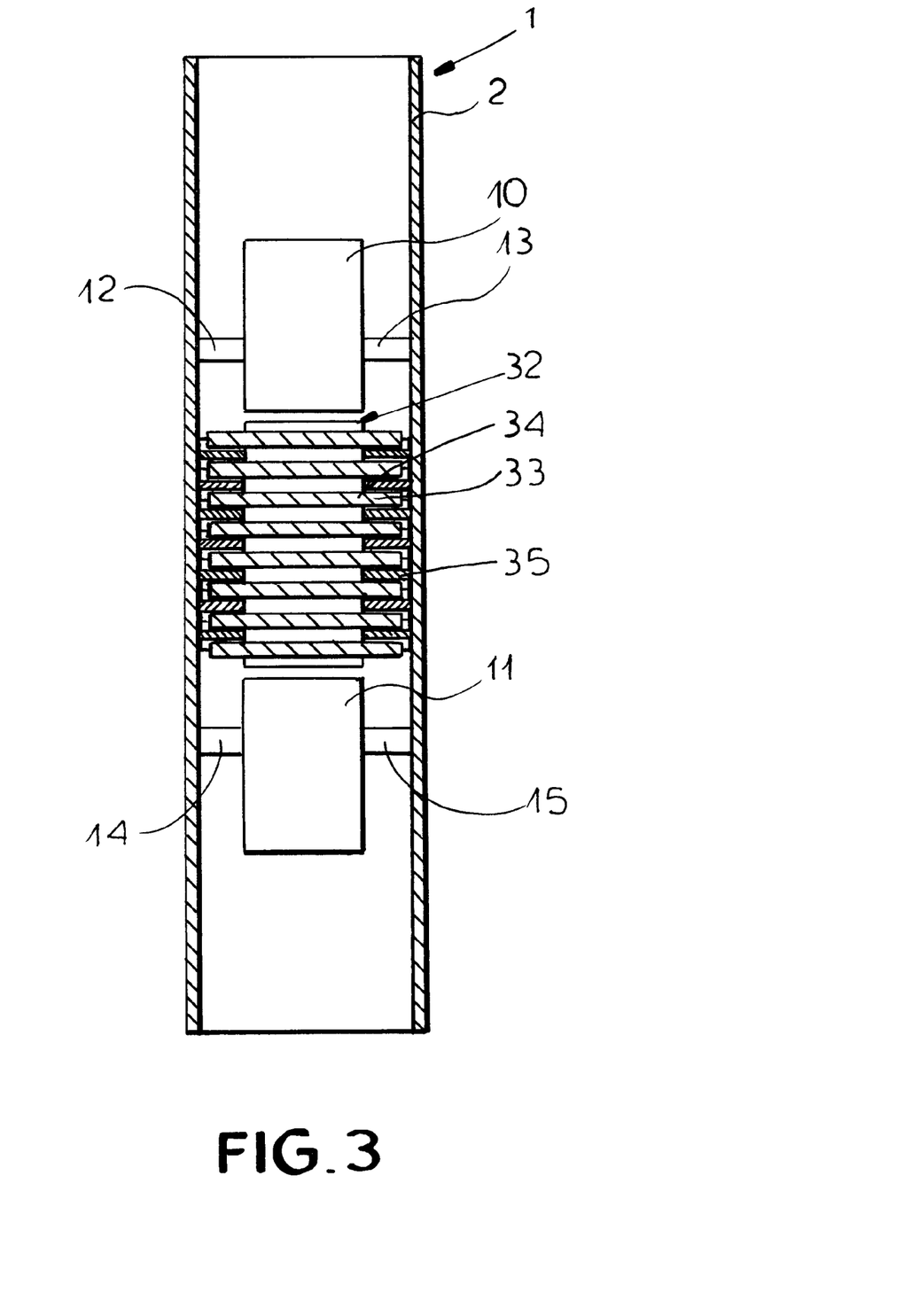
FIG. 3 is a longitudinal section through the combination of rotor and support tube of a third embodiment for a pump.
Figure 4:
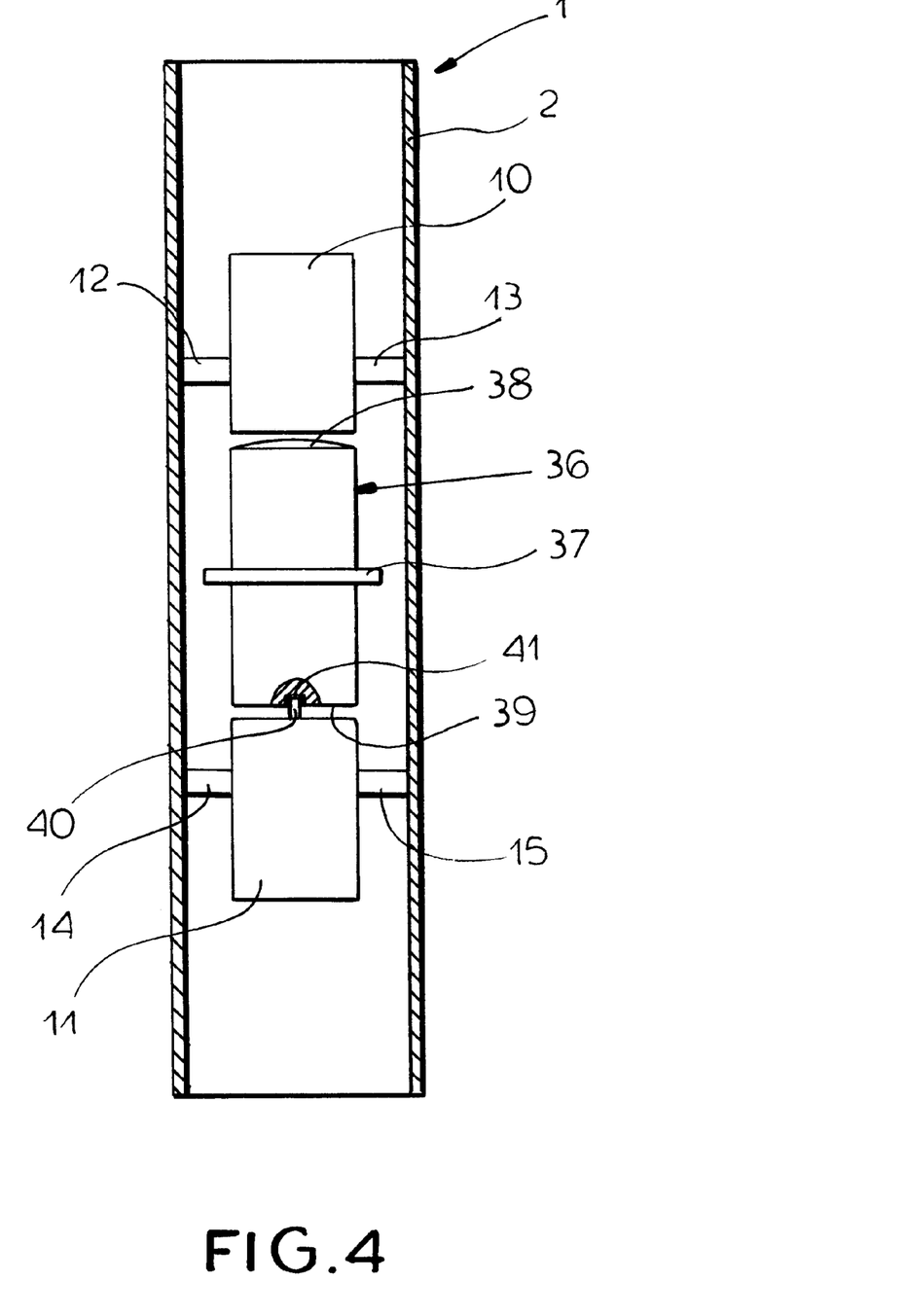
FIG. 4 is a longitudinal section through the combination of support tube and rotor in a fourth embodiment for a pump.

The embodiments of FIGS. 2–4 differ from that of FIG. 1 only by different shapes of the rotor, whereby parts lying externally of the support tube 2 are identical with those of the embodiment according to FIG. 1 and have been omitted for clarity. In FIGS. 2–4 those parts which have been already given reference numerals for FIG. 1 have the same configuration and/or function in the embodiments of FIGS. 2–4.

In FIG. 2 the rotor 30 has an outer diameter which corresponds approximately to the inner diameter of the support tube 2. In its outer surface screw-like channels, identified at 31, for example, are formed in the rotor. The rotor 30 can be set into rotation by the synchronous motor comprised of the rotary field stator 28 and poled wheel magnet 9 and is effective as a displacement pump. Such a rotor device 1 can be used for generating high vacuum.

In the embodiment according to FIG. 3, a rotor 32 with eight spaced-apart scoop-shaped blades in a crown, designated for example at 33, has been shown for example comprised of a plurality of individual blades as indicated for example at 34. In the spaces between the blade crown 33 the blade crowns of the support tube 4 extend as has been indicated for example at 35. They also are comprised of individual blades. The blade crowns 33 and 35 form the flow creating parts of a turbocompressor. Upon driving of the rotor 32 by means of the synchronous motor composed of the rotary field stator 28 and the pole wheel magnet 29, the displacement of a gaseous medium by the turbocompressor can be effected.

In the embodiment of FIG. 4, a rotor 36 is provided whose outer contours differ from those of the rotor 3 of FIG. 1 only in that they have substantially smooth cylindrical surfaces in their center which is provided with an outwardly projecting annular rib 37. The vanes for displacing the fluid have been omitted.

To avoid a mechanical contact of regions of the rotor 36 spaced from the axis, the rotor has a spherically configured end 38. To the extent that a contact between the rotor 36 and the radial stabilizer 10 occurs, the area of the contact is the region of the center and involves a surface of low peripheral speed. It will be self-understood that the lower end can be correspondingly spherically configured.

The lower radial stabilizer 37 has at its axial center a bearing pin 40 which extends toward the neighboring end of the rotor 36 and in which the bearing recess 41 is formed. Between the bearing pin 40 and the bearing recess 41 there is a play sufficient to enable normal radial deflection of the rotor 36 without the pin and the recess from coming into contact only in a case that the radial deflection is excessive will the pin 40 and the recess 41 limit further radial movement. Such a radial bearing can, it will be understood, also be provided at the upper radial stabilizer 10.

Figure 5:
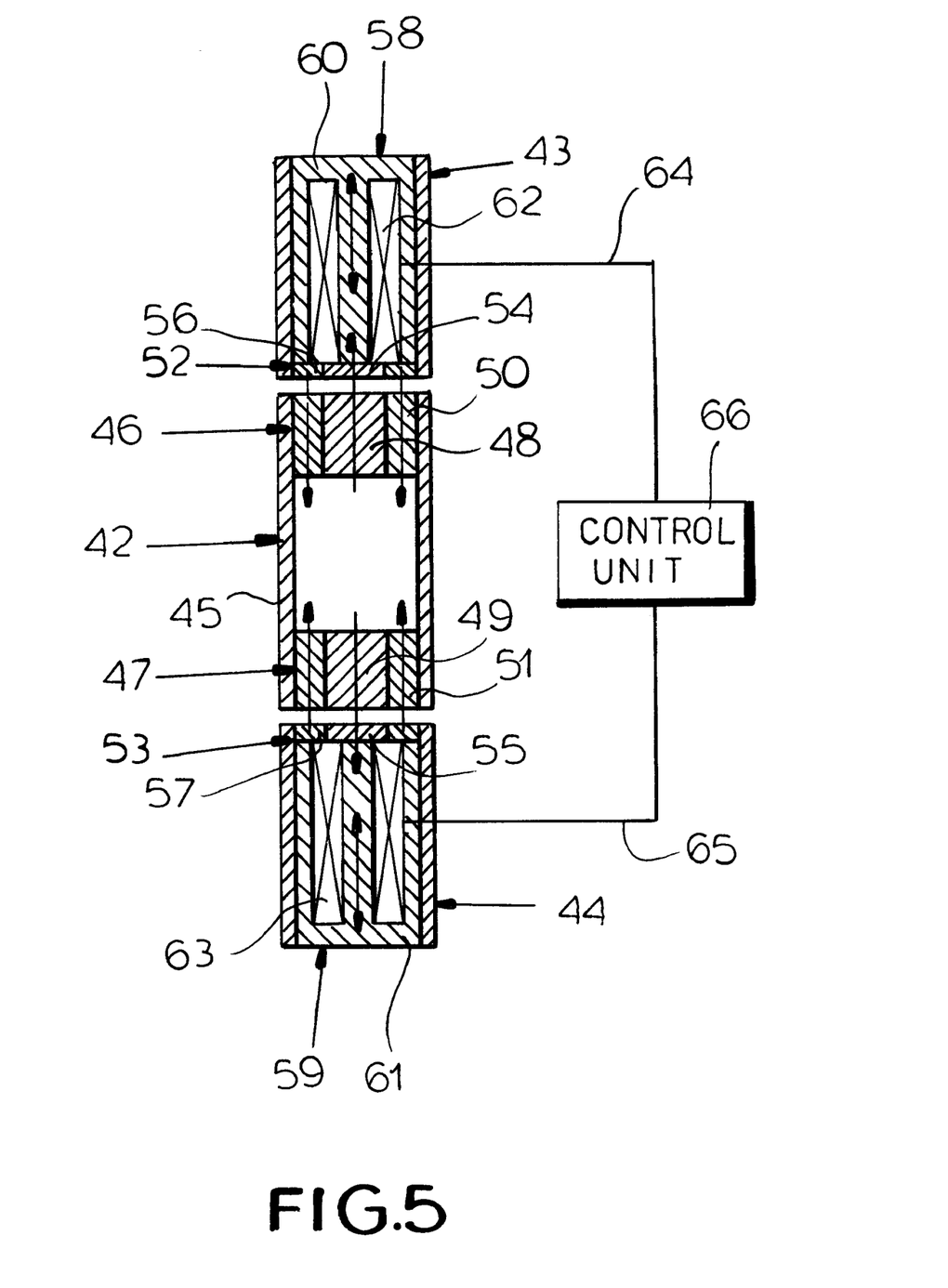
FIG. 5 is a longitudinal section through the combination of rotor hub and radial stabilizers in a fifth embodiment.

In the embodiment according to FIG. 5, the support tube 2 with all of its associated parts has been omitted for the sake of clarity. FIG. 5 shows a rotor 42 which is held magnetically between two radial stabilizers 43, 44. The rotor 42 has an outwardly smooth rotor hub 45 which is circular in cross section and whose cross section is extended by the radial stabilizers 43, 44. Not indicated in FIG. 5 are the ribs 12, 13, 14, 15 (FIG. 1) with which the radial stabilizers 43, 44 are affixed on the inner side of the support tube 2 and also not shown are the vanes 5, 6 for displacement of the fluid.

The rotor 42 has at its ends respective rotor magnets 46, 47. Both rotor magnets 46, 47 are of bipartite construction. They each are comprised of a cylindrical inner magnet 48, 49 and an outer magnet 50, 51 respectively surrounding same. The outer magnets 50, 51 lie in their inner sides against the neighboring inner magnets 48, 49.

The rotor magnets 46, 47 are juxtaposed each respectively with a stator magnet 52, 53. The stator magnets 52, 53 are identically bipartite in the same manner as the rotor magnets 46, 47, i.e. they each have a cylindrical inner magnet 54, 55 and an outer magnet 56, 57 surrounding same, lying against it and likewise formed in a ring. The diameters of the inner magnets 54, 55 of the stator magnets 52, 53 correspond to the diameters of the inner magnets 48, 49 of the rotor magnets 46, 47 while the diameters of the outer magnets 52, 53 are equal to the diameters of the outer magnets 50, 51 of the rotor magnets 46, 47. They are all coaxially arranged.

The rotor magnets 46, 47 and the stator magnets 52, 53 are so magnetized that the respective neighboring pairs of magnets which are opposite one another over their entire areas attract one another. The special character of the present invention resides in that respective pairs of opposing inner magnets 48, 54 or 49, 55 are magnetized axially away from the rotor 42 while the respective pairs of juxtaposed outer magnets 50, 56 or 51, 57 are axially magnetized in the direction toward the rotor 42, i.e. oppositely. The opposite magnetization increases stiffness of the journaling of the rotor in the rotary direction very substantially.

In the radial stabilizers 43, 44, cup coils 58, 59 are disposed which are each comprised of a cup-shaped ferromagnetic yoke 60, 61 and an electric coil 62, 63 therein. The yokes 60, 61 are open toward the stator magnets 52, 53. The mean diameters of the coils 62, 63 correspond to the outer diameter of the respectively neighboring inner magnets 54, 55. Via electric conductors 64, 65, the coils 62, 63 are connected with a control unit 66. The control unit 66 feeds the coils 62, 63 with excitation current. Depending upon the direction of the current, the axial magnetic flux in the gap between the rotor 42 and radial stabilizers 43, 44 can be increased or weakened as has been indicated by the central double-headed arrow. As a result, the axial force effective in the gap is so varied that the rotor is always guided into the axial middle position between the radial stabilizers 43, 44.

What is claimed is:

1. A pump for a fluid comprising:
   a support tube;
   an elongated rotor rotatable in said support tube and having respective permanently magnetic rotor magnets at opposite ends of said rotor, and displacement elements on said rotor for displacing said fluid upon rotation of said rotor:
   means for radially suporting and positioning said rotor in said support tube and comprising:
   respective permanently magnetic stator magnets mounted on said support tube and juxtaposed with said rotor magnets in respective pairs, each stator magnet and rotor magnet pair being axially magnetized to attract and position said rotor radially within said tube solely with said permanent magnets;
   a magnetic axial stabilizer unit for stabilizing an axial position of said rotor in said tube; and
   an electric motor comprising a rotary-field-generating stator on said tube around said rotor, and a poleforming magnet on said rotor driven by said rotary field for rotating said rotor.

2. The pump defined in claim 1 wherein said rotor and stator magnets of each pair are each comprised of two magnet parts fitting one inside another and of opposite polarization directions, the juxtaposed magnet parts of each pair being magnetized oppositely.

3. A pump for a fluid comprising:
   a support tube;
   an elongated rotor rotatable in said support tube and having displacement elements on said rotor for displacing said fluid through said support tube upon rotation of said rotor;
   means for radially suporting and positioning said rotor in said support tube and comprising:
   at each end of said rotor a respective pair of axially juxtaposed members including an axially polarized permanent magnet and a flux guide piece axially attracted thereto, one of the members of each pair being affixed to a respective end of the rotor and the other member of the respective pair being fixed in said tube, whereby said rotor is axially suspended magnetically between said pairs, said rotor being radially positioned within said tube solely with said permanent magnets;
   a magnetic axial stabilizer unit for stabilizing an axial position of said rotor in said tube; and
   an electric motor comprising a rotary-field-generating stator on said tube around said rotor, and a poleforming magnet on said rotor driven by said rotary field for rotating said rotor.

4. The pump defined in claim 3, further comprising electromagnetic coils for reinforcing magnetization of said flux guide pieces to increase attractive force between said magnets and the flux guide pieces of said pairs.

5. The pump defined in claim 4 wherein said other members of each pair are received in radial stabilizers having contours which do not extend outwardly beyond said rotor hub.

6. The pump defined in claim 5 wherein the juxtaposed members of at least one of said pairs have confronting spherical configurations.

7. The pump defined in claim 5 wherein the juxtaposed members of at least one of said pairs have a bearing pin fitting into a bearing recess.

8. The pump defined in claim 5 wherein the juxtaposed member of said pairs are directly opposite one another.

9. The pump defined in claim 5 wherein said magnetic axial stabilizer unit includes at least one electromagnet coil, a control device connected with said coil and a sensing means for an axial position of said rotor and connected with said control device for regulating current flow in said coil such that a magnetic field of said coil counteracts an axial movement of said rotor from a predetermined position.

10. The pump defined in claim 9 wherein said magnetic axial stabilizer unit has two electromagnetic coils arranged respectively proximal to said others of said members of said pairs.

11. The pump defined in claim 10 wherein said coils surround said support tube.

12. The pump defined in claim 10 wherein said coils are received in said radial stabilizers.

13. The pump defined in claim 12 wherein said radial stabilizers receive respective flux guide pieces and magnetic fields of said flux guide pieces and of said coils are superimposed in gaps at the ends of said rotor.

14. The pump defined in claim 13 wherein said flux guide pieces are arranged at levels of the respective coils.

15. The pump defined in claim 5 wherein said rotor is a pulse generator and said support tube is a pulse pickup, the pulse generator producing pulses for the pulse pickup corresponding to the rotation of said rotor.

16. The pump defined in claim 15 wherein the pulse generator is formed as at least one pulse magnet and said pulse pickup is a coil juxtaposed with the pulse magnet.

17. The pump defined in claim 5 wherein said rotary field generator stator is fed with three-phase current and said pole-forming magnet is radially magnetized.

18. The pump defined in claim 17 wherein said poleforming magnet has at least four magnetic segments magnetited in different radial directions.

19. The pump defined in claim 18 wherein said rotary field generating stator is connected with an electronic three-phase generator having load-angle regulation.

20. The pump defined in claim 3 wherein said rotor is an axial displacement impeller.

21. The pump defined in claim 3 wherein said rotor has a rotor hub, said one members of said pairs being secured to said rotor hub and said other members of each pair being juxtaposed with ends of said rotor hub.

22. The pump defined in claim 3 wherein said support tube or said rotor is formed with a screw-shaped rib forming a helical channel.

23. The pump defined in claim 3 wherein said rotor is formed with scoop-shaped blades interdigitating with scoop crowns on an inner wall of the support tube.

* * * * *